US00PP17202P2

(12) United States Plant Patent
Pieters

(10) Patent No.: US PP17,202 P2
(45) Date of Patent: Nov. 14, 2006

(54) ***CHRYSANTHEMUM* PLANT NAMED 'GEDI THREE GEN'**

(50) Latin Name: *Chrysanthemum morifolium*
Varietal Denomination: GEDI THREE GEN

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 108 days.

(21) Appl. No.: 11/112,939

(22) Filed: Apr. 22, 2005

(51) Int. Cl.
*A01H 5/00* (2006.01)

(52) U.S. Cl. ..... Plt./288

(58) Field of Classification Search ..... Plt./288
See application file for complete search history.

(56) References Cited

U.S. PATENT DOCUMENTS

PP13,102 P2 10/2002 Pieters
PP13,885 P2 6/2003 Pieters

*Primary Examiner*—Kent Bell
*Assistant Examiner*—Annette H Para
(74) *Attorney, Agent, or Firm*—Knobbe, Martens, Olson & Bear, LLP

(57) ABSTRACT

A new and distinct *Chrysanthemum* plant cultivar is disclosed, characterized by flowers having white ray florets with a slightly creamy center. The plant naturally blooms in the last two weeks of August. The plants are freely branching, and have a round and mounding growth habit.

1 Drawing Sheet

Figure 1:
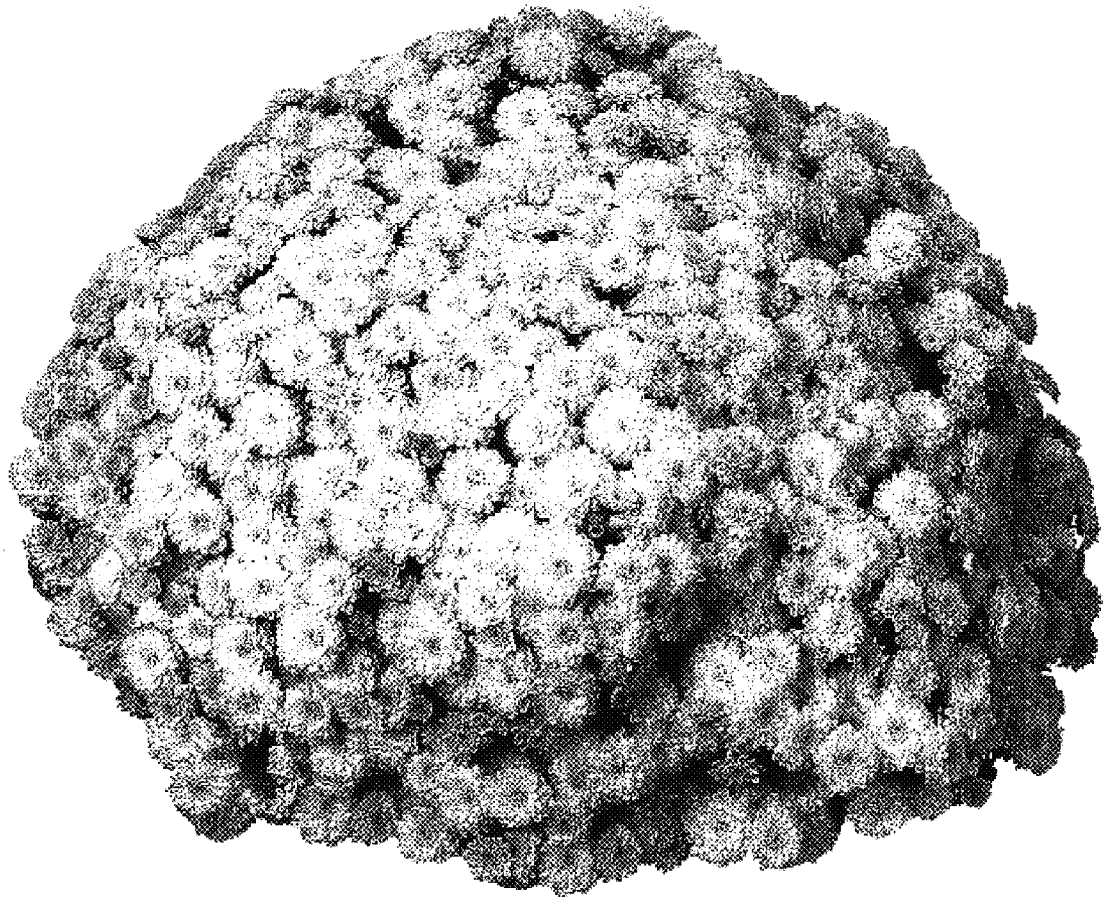

Latin name of the genus and species: *Chrysanthemum morifolium.*
Variety denomination: 'GEDI THREE GEN'.

BACKGROUND OF THE INVENTION

The new cultivar is a product of hybridization of an undistributed female parent *Chrysanthemum* plant variety '95 136 74' (unpatented) and a male parent *Chrysanthemum* plant variety 'GEDI ONE TER' (U.S. Plant Pat. No. 13,885). The new cultivar was discovered and selected by Dirk Pieters in Oostnieuwkerke, Belgium, in September, 1999.

Asexual reproduction of the new cultivar by tissue culture and terminal cuttings was performed in Oxnard, Calif., and has shown that the unique features of this cultivar are stable and reproduced true to type on successive generations.

SUMMARY OF THE INVENTION

The cultivar 'GEDI THREE GEN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GEDI THREE GEN.' These characteristics in combination distinguish 'GEDI THREE GEN' as a new and distinct *Chrysanthemum* cultivar:

1. The flower has white ray florets with a slightly creamy center.
2. The plant has a round and mounding growth habit.
3. The plant is freely branching.
4. The plant exhibits average vigor.
5. The plant naturally blooms beginning the last two weeks of August.

Plants of the new cultivar are similar to plants of the female parent variety, '95 136 74' in most horticultural characteristics, however plants of the new cultivar have larger diameter flowers that are longer lasting than the flowers of the female parent variety '95 136 74.' Plants of 'GEDI THREE GEN' have a more round growth habit than the plants of the female parent '95 136 74.' Additionally, plants of 'GEDI THREE GEN' are taller than the female parent variety.

Plants of the new cultivar 'GEDI THREE GEN' are similar to plants of the male parent variety, 'GEDI ONE TER,' in most horticultural characteristics, however plants of the new cultivar are more flexible, and have a more round plant growth habit than plants of the male parent variety. Additionally, plants of the new cultivar 'GEDI THREE GEN' naturally bloom approximately two to four weeks earlier than plants of the male parent variety 'GEDI ONE TER.'

In comparison to the commercially available variety 'FLORENCE' (U.S. Plant Pat. No. 13,102), the new variety 'GEDI THREE GEN' has approximately 11 more flowers per flowering branch. Additionally, the new variety 'GEDI THREE GEN' blooms approximately two to three weeks earlier than the comparable variety 'FLORENCE.' The floral longevity of the new variety is about 11 days longer than the comparable variety. The flowers of the new variety 'GEDI THREE GEN' have fewer ray florets than the comparable variety.

BRIEF DESCRIPTION OF THE PHOTOGRAPH

The accompanying photograph in FIG. 1 illustrates in full color a typical plant of 'GEDI THREE GEN' grown in a 2 gallon container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GEDI THREE GEN' plants grown in a greenhouse in Oxnard, Ventura County, Calif., during the month of September, 2003. The growing temperature ranged from about 12° C. to 15° C. at night to about 12° C. to 20° C. during the day. Measurements and numerical values represent averages of typical flowering types, and are believed to apply to plants of the variety grown under similar conditions of soil and climate elsewhere:

Botanical classification: *Chrysanthemum morifolium* 'GEDI THREE GEN.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceious perennial.
Height: Approximately 28.5 cm.
Plant spread: Approximately 33 cm.
Growth rate: Moderate.
Branching characteristics: Free branching.
Length of lateral branches: Approximately 23 cm.
Number of leaves per lateral branch: Approximately 15.
Age of plant described: Approximately 135 days from a rooted cutting.

FOLIAGE

Leaf:
*Arrangement.*—Alternate.
*Average length.*—Approximately 6.2 cm.
*Average width.*—Approximately 5.3 cm.
*Shape of blade.*—Ovate.
*Apex.*—Cuspidate.
*Base.*—Attenuate.
*Attachment.*—Stalked.
*Margin.*—Palmately lobed and toothed.
*Texture of top surface.*—Lightly pubescent.
*Texture of bottom surface.*—Lightly pubescent.
*Leaf internode length.*—Approximately 3.1 cm.
*Color.*—Young foliage upper side: Near Green 138A. Young foliage under side: Near Green 138B. Mature foliage upper side: Near Green 137A. Mature foliage under side: Near Green 138A. Venation upper side: Near Green 138B. Venation under side: Near Green 138B. Type: Palmately net.

Petiole:
*Average length.*—Approximately 2.1 cm.
*Color.*—Near Green 138A.
*Diameter.*—Approximately 0.2 cm.

BLOOM

Flower:
*Flowering habit.*—Induced by darkness period greater than approximately 13.5 hours, approximately 45 days of appropriate day length required to induce and develop blooms.
*Form.*—Decorative.
*Natural flowering season.*—Approximately the last week of August through the first week of September.
*Number of flowers per lateral branch.*—Approximately 22.
*Diameter.*—Approximately 5.9 cm.
*Depth.*—Approximately 2.3 cm.
*Longevity on plant.*—Approximately 29 days.
*Persistence.*—Persistent.

Ray florets:
*Appearance.*—Matte.
*Texture.*—Smooth.
*Average number of ray florets per flower.*—Approximately 180.
*Shape.*—Oblong.
*Aspect.*—Flat.
*Margin.*—Entire.
*Apex.*—Retuse.
*Length.*—Approximately 2.8 cm.
*Width.*—Approximately 1 cm.
*Color.*—Upper surface at first opening: Near Yellow 11B. Upper surface at maturity: Near White 155D. Upper surface at fading: Near White 155D. Under surface at first opening: Near Yellow 11C. Under surface at maturity: Near White 155D. Under surface at fading: Near White 155D.

Disc florets:
*Appearance.*—Shiny.
*Texture.*—Smooth.
*Average number of disc florets per disc.*—Approximately 20.
*Shape.*—Cylindric.
*Apex.*—Obtuse.
*Average length.*—Approximately 0.8 cm.
*Average width.*—Approximately 0.1 cm.
*Color.*—At first opening: Near Yellow 11B. At maturity: Near Yellow 11C. At fading: Near Yellow 12D.

Peduncle:
*Length.*—At terminal end (shortest): Approximately 3.4 cm. At lateral end (longest): Approximately 6.7 cm.
*Angle to stem.*—Acute.
*Strength.*—Moderate.
*Color.*—Near Green 138A.
*Habit.*—Upright.
*Diameter.*—Approximately 0.2 cm.
*Surface texture.*—Lightly pubescent.

Flower bud:
*Length.*—Approximately 1 cm.
*Diameter.*—Approximately 0.8 cm.
*Form.*—Globular.
*Color.*—Near Yellow 12D.

Involucral bracts (phyllaries):
*Appearance.*—Matte.
*Texture.*—Lightly pubescent.
*Number.*—Approximately 42.
*Shape.*—Oblanceolate.
*Margin.*—Entire.
*Apex.*—Acute.
*Length.*—Approximately 1.1 cm.
*Width.*—Approximately 0.9 cm.
*Color.*—Upper side: Near Green 138A. Under side: Near Green 138A.

REPRODUCTIVE ORGANS

Ray florets:
*Number of pistils per floret.*—1.
*Stigma shape.*—2 branched.
*Stigma color.*—Near Yellow 5D.
*Style color.*—Near Yellow 2D.
*Style length.*—Approximately 0.9 cm.
*Stamens:*—Absent.

Disc florets:

*Number of pistils per floret.*—1.
*Stigma shape.*—Two-branched.
*Stigma color.*—Near Yellow 5D.
*Style length.*—Approximately 0.3 cm.
*Style color.*—Near Yellow-green 154D.
*Number of stamens per floret.*—Approximately 5.
*Anther shape.*—Tubular.
*Anther color.*—Near Yellow 6A.
*Pollen color.*—Pollen not detected.

OTHER CHARACTERISTICS

Disease resistance: Neither resistance nor susceptibility has been observed.

Drought tolerance/cold tolerance: Flowering plants are hardy to low temperature of about −2° C. Non-flowering plants are hardy in the approximate range of 3° C. to −6° C., depending upon duration of cold an amount of moisture in the soil. With adequate water, the plants are hardy to a high temperature of about 45° C.

Fruit/seed production: Commercially, this plant is not used or observed in a stage wherein seeds would be produced. Therefore, seed production has not been observed.

What is claimed is:

1. A new and distinct cultivar of *Chrysanthemum* plant named 'GEDI THREE GEN' as herein illustrated and described.

* * * * *